United States Patent [19]
Baker et al.

[11] Patent Number: 5,789,573
[45] Date of Patent: Aug. 4, 1998

[54] ANTISENSE INHIBITION OF ICAM-1, E-SELECTIN, AND CMV IE1/IE2

[75] Inventors: Brenda Baker; C. Frank Bennett; Kevin P. Anderson, all of Carlsbad, Calif.

[73] Assignee: Isis Pharmaceuticals, Inc., Carlsbad, Calif.

[21] Appl. No.: 653,653

[22] Filed: May 24, 1996

Related U.S. Application Data

[63] Continuation-in-part of Ser. No. 440,740, May 12, 1995, and Ser. No. 927,506, Nov. 19, 1992, Pat. No. 5,591,720, which is a continuation-in-part of Ser. No. 568,366, Aug. 16, 1990, abandoned, said Ser. No. 440,740, is a continuation-in-part of Ser. No. 063,167, May 17, 1993, Pat. No. 5,514,788, which is a continuation-in-part of Ser. No. 007,997, Jan. 21, 1993, Pat. No. 5,591,623, which is a continuation-in-part of Ser. No. 939,855, Sep. 2, 1992, abandoned, which is a continuation-in-part of Ser. No. 567,286, Aug. 14, 1990, abandoned.

[51] Int. Cl.$^6$ .................... C07H 21/02; C07H 21/04; C12Q 1/68
[52] U.S. Cl. ............ 536/24.5; 536/23.1; 536/24.31; 536/24.33; 435/6; 435/91.1
[58] Field of Search ................ 514/44; 536/23.1, 536/24.5, 25.3; 435/6, 91.1, 325

[56] References Cited

U.S. PATENT DOCUMENTS

| | | | |
|---|---|---|---|
| 5,034,506 | 7/1991 | Summerton et al. | 528/391 |
| 5,378,825 | 1/1995 | Cook et al. | 536/25.34 |
| 5,585,479 | 12/1996 | Hoke et al. | 536/24.5 |

FOREIGN PATENT DOCUMENTS

| | | |
|---|---|---|
| WO 91/17755 | 11/1991 | WIPO . |
| WO 92/03139 | 3/1992 | WIPO . |
| WO 92/20823 | 11/1992 | WIPO . |
| WO 94/22488 | 10/1994 | WIPO . |
| WO 96/06621 | 3/1996 | WIPO . |

OTHER PUBLICATIONS

James, Towards gene inhibition therapy: a review of progress and prospects in the field of antiviral antisense nucleic acids and ribozymes, Antiviral Chemistry and Chemotherapy, vo. 2(4), pp.191–214, 1991.

Uhlmann et al., Antisense oligonucleotides: a new therapeutic principle, Chemical Reviews, vol. 90(4), pp. 543–584, Jun. 1990.

Tseng et al., Antisense oligonucleotide technology in the development of cancer therapeutics, Cancer Gene Therapy, vol. 1(1), pp. 65–71, Mar. 1994.

Gewirtz et al., Facility oligonucleotide delivery: helping antisense deliver on its promise, Proc. Natl. Acad. Sci., vol. 93, pp. 3161–3163, Apr. 1996.

Weiss et al., Upping the antisense ante, Science News, vol. 139, pp. 108–109, 1991.

Roush, Antisense aims for a renaissance, Science, vol. 276, pp. 1192–1193, May 1997.

Cory, S and Adams, J.M., "The Modified 5'-Terminal sequences in Messenger RNA of Mouse Myeloma Cells", *J. Mol. Biol.* 1975, 99, 519–547.

De Mesmaeker et al., "Antisense Oligonucleotides", *Acc. Chem. Res.* 1995, 28, 366–374.

Helene and Toulme, "Specific regulation of gene expression by antisense, sense and antigene nucleic acids", *Biochem. et Biophys. Acta* 1990, 1049, 99–125.

Kawasaki et al., "Uniformly Modified 2'–Deoxy'fluoro Phosphorothioate Oligonucleotides as Nuclease–Resistant Antisense Compounds with High Affinity and Specificity of RNA Targets", *J. Med Chem.* 1993, 36, 831–841.

Nielsen, P.E., et al., "Sequence–Selective Recognition of DNA by Strand Displacement with Thymine–Substituted Polyamide", *Science* 1991, 254, 1497.

Stenberg, R.M., Witte, P.R. and Stinski, M.F., "Multiple Spliced and Unspliced Transcripts from Human Cytomegalovirus Immediate–Early Region 2 and Evidence for a Common Initiation Site within Immediate–Early Region 1", *J. Virol.* 1985, 56, 665–675.

Stenberg, R.M., Thomsen, D.R., and Stinski, M.F., "Structural Analysis of the Major Immediate Early Gene of Human Cytomegalovirus", *J. Virol.* 1984, 49: 190–199.

*Primary Examiner*—John L. LeGuyader
*Assistant Examiner*—Andrew Wang
*Attorney, Agent, or Firm*—Law Offices of Jane Massey Licata

[57] ABSTRACT

Compositions and methods are provided for inhibiting the translation of a capped target mRNA. Antisense oligomers of the invention are targeted to the 5' cap region of the target mRNA and include oligonucleosides, PNAs, or oligonucleotides modified at the 2' position of the sugar. Preferably said oligomers inhibit protein translation directly via interference with ribosome assembly.

4 Claims, 4 Drawing Sheets

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

TCTGAGTAGC AGAGGAGCTC　　　　　　　　　　　　　　　　　　　　　　　　　　　2 0

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

TCTGAGTAGC AGAGGAGC　　　　　　　　　　　　　　　　　　　　　　　　　　　　1 8

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 3:

```
           GAAGTCAGCC AAGAACAGCT                                                           20
```

( 2 ) INFORMATION FOR SEQ ID NO: 4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 4:

```
           GUCAGAUCGC CUGGAGACGC C                                                         21
```

( 2 ) INFORMATION FOR SEQ ID NO: 5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 5:

```
           TGGCGTCTCC AGGCGATCTGA                                                          21
```

( 2 ) INFORMATION FOR SEQ ID NO: 6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 6:

```
           GGCGTCTCCA GGCGATCTGA C                                                         21
```

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 7:

```
           GGCGTCTCCA GGCGATCTGA                                                           20
```

( 2 ) INFORMATION FOR SEQ ID NO: 8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 8:

```
           TGGATGGCGT CTCCAGGCGA                                                           20
```

ANTISENSE INHIBITION OF ICAM-1, E-SELECTIN, AND CMV IE1/IE2

INTRODUCTION

The present application is a continuation-in-part application of U.S. patent application Ser. No. 08/440,740 filed on May 12, 1995 which is a continuation-in-part application of U.S. patent application Ser. No. 08/063,167 filed on May 17, 1993 now issued as U.S. Pat. No. 5,514,788, which is a continuation-in-part of U.S. patent application Ser. No. 08/007,997, filed Jan. 21, 1993, now issued U.S. Pat. No. 5,591,623, which in turn is a continuation-in-part of U.S. patent application Ser. No. 07/939,855, filed Sep. 2, 1992, now abandoned, which is a continuation-in-part of U.S. patent application 07/567,286, filed Aug. 14, 1990, now abandoned.

The present application is also a continuation-in-part of U.S. patent application Ser. No. 07/927,506 filed on Nov. 19, 1992, now issued U.S. Pat. No. 5,591,720, which is a continuation-in-part application of U.S. patent application Ser. No. 07/568,366 filed on Aug. 16, 1990, now abandoned.

FIELD OF THE INVENTION

This invention is directed to methods for inhibiting gene expression via interference with protein translation. The invention generally relates to the field of antisense inhibition of gene expression.

BACKGROUND OF THE INVENTION

Classical therapeutics have generally focused upon interactions with proteins in efforts to moderate their disease-causing or disease-potentiating functions. Such therapeutic approaches have many limitations. Recently, antisense therapeutic and diagnostic approaches have been demonstrated to be safe and effective.

Antisense methodology is the complementary hybridization of relatively short oligomers, usually oligonucleotides or oligonucleosides, to mRNA or DNA, such that the normal, essential functions of these target nucleic acids are disrupted. Hybridization is the sequence specific hydrogen bonding of nucleobases on the oligomer to RNA or single stranded DNA according to the rules of Watson-Crick base pairing. Members of such base pairs are said to be complementary to one another.

Considerable research is being directed to the application of oligonucleotides and other oligomers as antisense agents for therapeutic purposes. Oligonucleotides have already been employed as therapeutic moieties in the treatment of disease states in animals and man. Antisense oligomer compositions have been shown to be capable of modulating expression of genes implicated in viral, fungal and metabolic diseases. Further, antisense oligonucleotides have been safely administered to humans and clinical trials of approximately a dozen antisense drugs, targeted to viral and cellular gene products, have been initiated.

The present invention provides new antisense compounds and compositions together with methodologies for the use of certain antisense compounds for interfering with translation of selected mRNA targets.

Most antisense approaches utilize antisense oligonucleotides targeted to the AUG, or, less often, the 5'-untranslated region, 5' cap, 3'-untranslated region, coding or other regions of mRNA. Helene and Toulme, *Biochem. et Biophys. Acta* 1990, 1049, 99–125. It is also known to use antisense oligonucleotides which target the 5' cap of mRNA to interfere with mRNA function by equipping the oligonucleotides with cleaving moieties, as disclosed in PCT publication WO 91/17755 (Baker) and PCT publication WO 96/06621 (Adams and Reynolds), or by interfering with capping of nascent mRNA, as disclosed in PCT publication WO 94/22488 (Baker).

A number of antisense oligonucleotides have been found to elicit RNAse H activity. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis or Northern blotting showing a decrease in target mRNA abundance, and/or direct visualization of the cleavage products. Phosphorothioate oligodeoxynucleotides are substrates for RNAse H; however, some antisense oligomers, such as PNAs, oligonucleosides and oligonucleotides which are uniformly modified at the 2' position of the sugar, do not activate RNAse H. Kawasaki et al., *J. Med Chem.* 1993, 36, 831–841. Often a sequence which is highly active as a phosphorothioate oligodeoxynucleotide is inactive when made as an analog which is not a substrate for RNAse H. This may be true even if the affinity of the oligonucleotide for the target is increased by such a modification. Helene and Toulme, *Biochem. et Biophys. Acta* 1990, 1049, 109.

In the present invention, certain types of antisense oligomers which specifically hybridize to the 5' cap region of their target mRNA have been found to be surprisingly active in interfering with translation of the target mRNA into protein. These oligomers include peptide-nucleic acid (PNA) oligomers, oligonucleosides (such as those having an MMI, amide or morpholino backbone) and oligonucleotides having modifications at the 2' position of the sugar. These oligomers are believed to act in an RNAse H-independent fashion to inhibit translation of the target mRNA directly. This is believed to occur via interference with ribosome assembly on the target mRNA.

SUMMARY OF THE INVENTION

This invention provides methods for inhibiting the translation of a selected capped target mRNA by contacting the target mRNA with an antisense oligomer which is 8–25 bases in length and which is complementary to the 5' cap region of the target mRNA. The oligomer may be a 2'-modified oligonucleotide, an oligonucleoside, or a peptide-nucleic acid oligomer. Preferred 2' modifications include 2'-OCH$_2$CH$_2$OCH$_3$, 2'-OCH$_3$, 2'-OCH$_2$CH$_2$CH$_3$, 2'-OCH$_2$CH$_2$=CH$_2$ and 2'-F modifications, with 2'-OCH$_2$CH$_2$OCH$_3$ modifications being more preferred. Preferred oligonucleosides include those having morpholino, amide or MMI internucleoside linkages. Peptide-nucleic acid oligomers are also preferred.

In the present invention, certain types of antisense oligomers which specifically hybridize to the 5' cap region of their specific target mRNA have been fount to be surprisingly active in interfering with translation of the target mRNA into protein. These oligomers include peptide-nucleic acid (PNA) oligomers, oligonucleosides (such as those having an amide, morpholino or MMI backbone) and oligonucleotides having 2'-modifications. These oligomers are designed to be specifically hybridizable with the 5' cap region of the target mRNA.

BRIEF DESCRIPTION OF THE DRAWINGS

FIG. 1 is a set of line graphs showing the reduction of ICAM-1 protein levels by 2' modified oligomers targeted to the 5' cap of ICAM-1.

DETAILED DESCRIPTION OF THE INVENTION

Figure 1A:
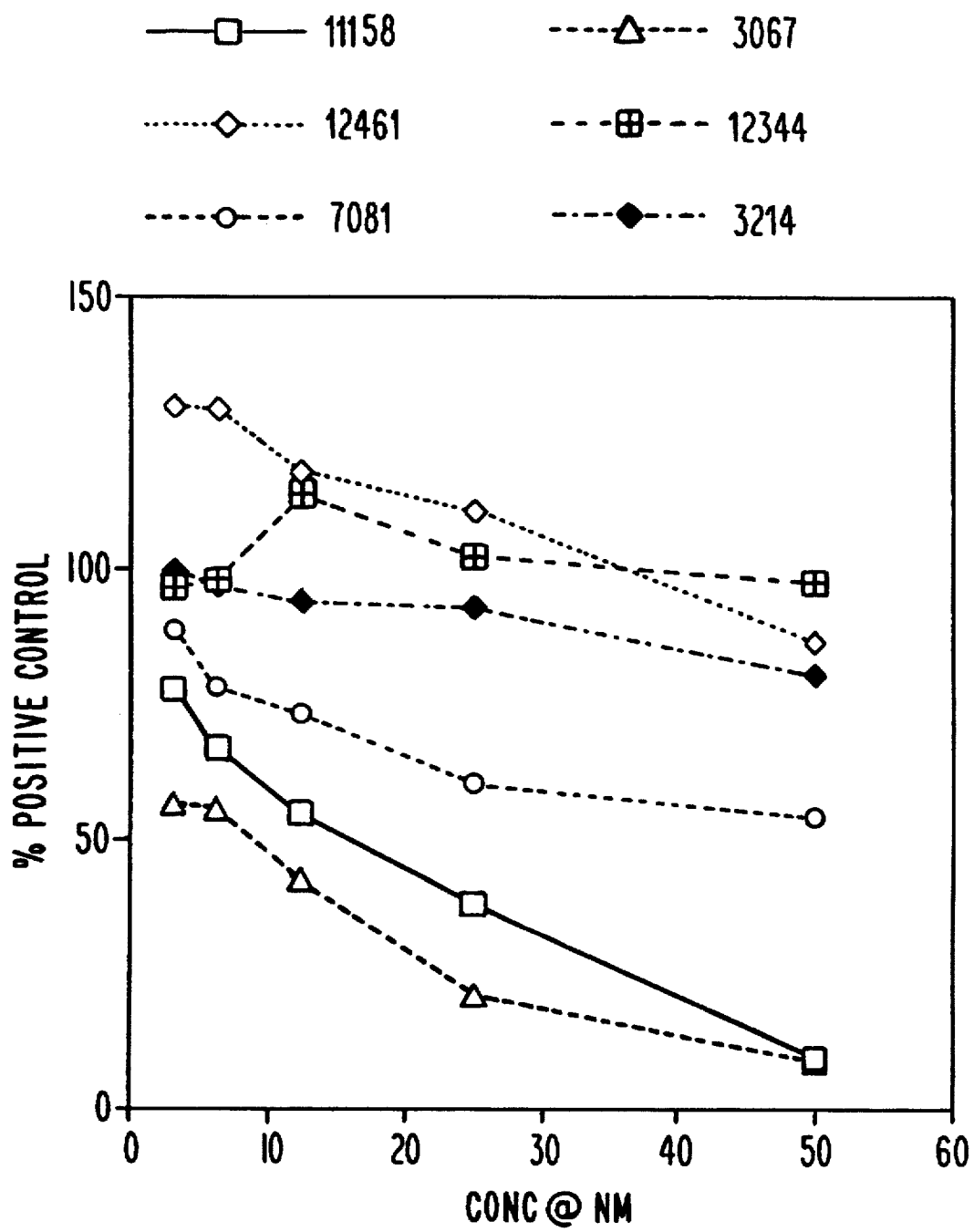
FIG. 1A shows the activity of phosphodiester compounds.

It has been recognized that the majority of eukaryotic and viral RNAs and messenger RNAs have a unique chemical structure at their 5' terminus which is required in varying degrees for their maturation, stability, and efficiency of translation. The general structural features are given in S. Cory and J M Adams, *J. Mol. Biol.* 1975, 99, 519–547. The cap is a guanosine residue which is methylated at the nitrogen 7 position. It is joined to the 5'-most transcribed nucleotide of the RNA via a triphosphate linkage between the 5' hydroxyl groups of each residue.

The antisense oligomers in accordance with this invention specifically hybridize with a capped target MRNA transcript at its 5' end. Preferably, the oligomers will bind to a region including at least one of the first 20 nucleotides at the 5' end of the target mRNA, where the first nucleotide is adjacent to the 5' cap and connected to the methylated guanosine of the cap via the triphosphate linkage described supra. More preferably, the oligomers will bind to a region including at least one of the first five nucleotides at the 5' end of the target mRNA. The oligomers of the present invention preferably are from about 5 to about 50 bases in length. Oligomers from about 8 to 25 bases in length are more preferred.

In the context of this invention, the term "oligomer" is intended to encompass oligonucleotides, oligonucleotide analogs, oligonucleosides or oligonucleotide-mimicking macro-molecules, all of which have heterocyclic bases (nucleobases) positioned thereon which are capable of specifically hybridizing to a complementary base sequence. This term includes oligomers consisting of naturally occurring bases, sugars and intersugar (backbone) linkages, as well as oligomers having non-naturally occurring portions which function similarly. Such modified or substituted oligomers are often preferred over native forms because of properties such as, for example, enhanced cellular uptake, increased stability in the presence of nucleases and/or increased affinity for a complementary target sequence. Affinity of an oligonucleotide for its target is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target.

Specific examples of some preferred oligomers envisioned for this invention are oligonucleosides, which contain non-phosphorus intersugar linkages, for example short chain heteroatomic or heterocyclic intersugar linkages. Most preferred are those with $CH_2$—NH—O—$CH_2$, $CH_2$—N($CH_3$)—O—$CH_2$ [known as the methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). These and other preferred backbones are disclosed in WO 92/20823 and U.S. Pat. No. 5,378,825, both of which are coassigned to the assignee of the present invention and are incorporated herein in their entirety. Other preferred nitrogen-containing backbones are the amide backbones of De Mesmaeker et al., *Acc. Chem. Res.* 1995, 28, 366–374. Of these, $CH_2$—CO—NR—$CH_2$, also called amide-3, and $CH_2$—NH—CO—$CH_2$, also called amide-4, are more preferred. Also preferred are oligomers having morpholino backbone structures (Summerton, J. E. and Weller, D. D., U.S. Pat. No. 5,034,506). In other preferred embodiments, such as the peptide-nucleic acid (PNA) backbone, the phosphodiester backbone of a native oligonucleotide may be replaced with a polyamide backbone, the bases being bound directly or indirectly to the aza nitrogen atoms of the polyamide backbone (P. E. Nielsen, M. Egholm, R. H. Berg, O. Buchardt, *Science* 1991, 254, 1497). Other preferred oligomers are oligonucleotides having modifications at the 2' position of the sugar moiety. Some examples of suitable 2' modifications are $C_1$ to $C_{10}$ lower alkyl, substituted lower alkyl, alkoxyalkoxy, alkaryl or aralkyl; F; Cl; Br; CN; $CF_3$; $OCF_3$; O—, S—, or N-alkyl; SH, $SCH_3$, OCN, alkylamines such as $O(CH_2)_nNH_2$ where n is from 1 to about 10; $O(CH_2)_nCH_3$ where n is from 1 to about 10; or other groups which improve the pharmacokinetic or pharmacodynamic properties of the oligomer or the affinity of the oligomer for its target, or which stabilize the oligomer. Presently, more preferred oligomers include MMI and morpholino oligonucleosides, PNAs, 2'-O-alkyl and 2'-alkoxyalkoxy oligonucleotides, most preferably, 2'-$OCH_2CH_2OCH_3$ [also known as 2'-O-(2-methoxyethyl) or 2'-methoxyethoxy]. It is not necessary that the oligomer be uniformly modified in the aforementioned way(s).

Many of the oligomers used in accordance with this invention may be conveniently and routinely made through the well-known technique of solid phase synthesis. Equipment for such synthesis is sold by several vendors including Applied Biosystems. Any other means for solid or liquid phase synthesis may also be employed; synthesis of the oligomers is well within the talents of the routineer. It is well known to use these techniques to prepare 2'-modified oligonucleotides, backbone-modified oligomers and other oligomers.

In the methods of the invention, a capped target mRNA is contacted with an oligomer. In the context of this invention, a "target" mRNA is the mRNA whose translation is to be specifically inhibited through antisense interaction. The antisense oligomers of the invention are designed to be specifically hybridizable with a complementary nucleotide sequence on their mRNA target. The term "target" or "target region" also encompasses this sequence of the mRNA, i.e., the particular region to which the antisense oligomer is complementary. In the context of this invention, to "contact" a target mRNA with an oligomer means to add the oligomer, either in vitro or ex vivo, to a cell suspension or tissue sample containing or suspected of containing said target mRNA, or to administer the oligomer to cells or tissues within an animal which contain or are suspected to contain the target mRNA. The oligomer is usually in a liquid carrier or part of a pharmaceutical composition which may contain additional ingredients in addition to carrier.

"Hybridization", in the context of this invention, means hydrogen bonding, also known as Watson-Crick base pairing, between complementary nucleobases. Guanine and cytosine are examples of complementary bases which are known to form three hydrogen bonds between them. Adenine and thymine are examples of complementary bases which form two hydrogen bonds between them. Triple-strand formation, or triplexing, is a particular form of hybridization of an oligomer to a double-stranded region of the target, such as a hairpin region on an RNA molecule. "Specifically hybridizable" and "complementary" are terms which are used to indicate a sufficient degree of complementarity such that stable and specific binding occurs between the RNA target and the oligomer. It is understood that an oligomer need not be 100% complementary to its target nucleic acid sequence to be specifically hybridizable. An oligomer is specifically hybridizable when binding of the oligomer to the target interferes with the normal function of the target molecule to cause a loss of utility, and there is a sufficient degree of complementarity to avoid non-specific binding of the oligomer to non-target sequences under conditions in which specific binding is desired, i.e., under physiological conditions in the case of in vivo assays or therapeutic treatment, or, in the case of in vitro assays, under conditions in which the assays are conducted.

The oligomers of the invention are designed to be specifically hybridizable with the 5' cap region of a capped target mRNA. As herein defined, "5' cap region" refers to the region of said target mRNA which includes at least one of the first 20 bases at the 5' terminus of said target mRNA. In other words, at least one of nucleotides 1-20 where nucleotide number 1 is adjacent to the cap structure. It is preferred that the oligomers be specifically hybridizable with a region of the target mRNA which includes at least one of the first five nucleotides at the 5' terminus of the target mRNA.

The following are instances in which the methods and compositions of the present invention have been used effectively. The present invention is not limited to these targets or these compositions.

A number of oligomers which target the human intercellular adhesion molecule-1 (ICAM-1) mRNA transcript have been evaluated for activity at reducing ICAM-1 expression in human vascular endothelial cells. ICAM-1 is one of several cell adhesion molecules expressed on the surface of vascular endothelium and participates in a variety of immune and inflammatory responses. ICAM-1 is also expressed on non-endothelial cells in response to inflammatory mediators. Elevated levels of ICAM-1 expression have been observed in a number of disease states such as rheumatoid arthritis and psoriasis, and ICAM-1 has become a target of therapeutic interest. Clinical trials are presently underway for an antisense oligonucleotide that inhibits the expression of human ICAM-1, in patients with a variety of disease conditions: rheumatoid arthritis, ulcerative colitis, Crohn's disease, psoriasis and prevention of renal transplant rejection.

It has now been found that RNAse H activity is not necessary for good antisense activity when antisense oligomers are targeted to the 5' cap region of the ICAM-1 transcript. Surprisingly, oligomers which do not activate RNAse H, or at least are RNAse H-independent, have been found to be surprisingly active when targeted to this region. Data were obtained for fully 2'-modified oligomers which are not substrates for RNAse H. The target region was nucleotides 1-20 (where nucleotide 1 is immediately adjacent to the cap structure) of the ICAM-1 transcript. A dose response analysis of nine different oligomers was performed to determine their efficacy for inhibition of ICAM-1 cell surface protein expression in comparison to a phosphorothioate deoxyoligonucleotide, ISIS 3067 (SEQ ID NO: 1; TCTGAGTAGCAGAGGAGCTC), targeted to the same region. This compound had previously been shown to be very effective at inhibition of ICAM-1 expression. WO 92/03139 (Bennett et al.)

The oligomers studied were 2'-methoxy (also referred to as 2'-O-methyl), 2'-propoxy (also referred to as 2'-O-propyl), 2'-O-allyl, 2'-methoxyethoxy and 2'-fluoro analogs of this sequence with either a phosphorothioate (P=S) or phosphodiester (P=O) backbone. These compounds, listed in Table 1, were tested for their ability to reduce ICAM-1 protein levels in HUVEC cells. All compounds in Table 1 have the same sequence, SEQ ID NO: 1.

TABLE 1

| ISIS # | 2' modification | Backbone |
|---|---|---|
| 3061 | Deoxy (—H) | Phosphodiester (P=O) |
| 3214 | Methoxy (—OCH₃) | " |
| 7081 | Propoxy (—OCH₂CH₂CH₃) | " |
| 11158 | Methoxyethoxy (—OCH₂CH₂OCH₃) | " |
| 12461 | Allyl (—OCH₂CH=CH₂) | " |
| 3067 | Deoxy (—H) | Phosphorothioate (P=S) |
| 3224 | Methoxy (—OCH₃) | " |
| 11665 | Fluoro (—F) | " |
| 11159 | Methoxyethoxy (OCH₂CH₂OCH₃) | " |
| 12462 | Allyl (—OCH₂CH=CH₂) | " |

Figure 1B:
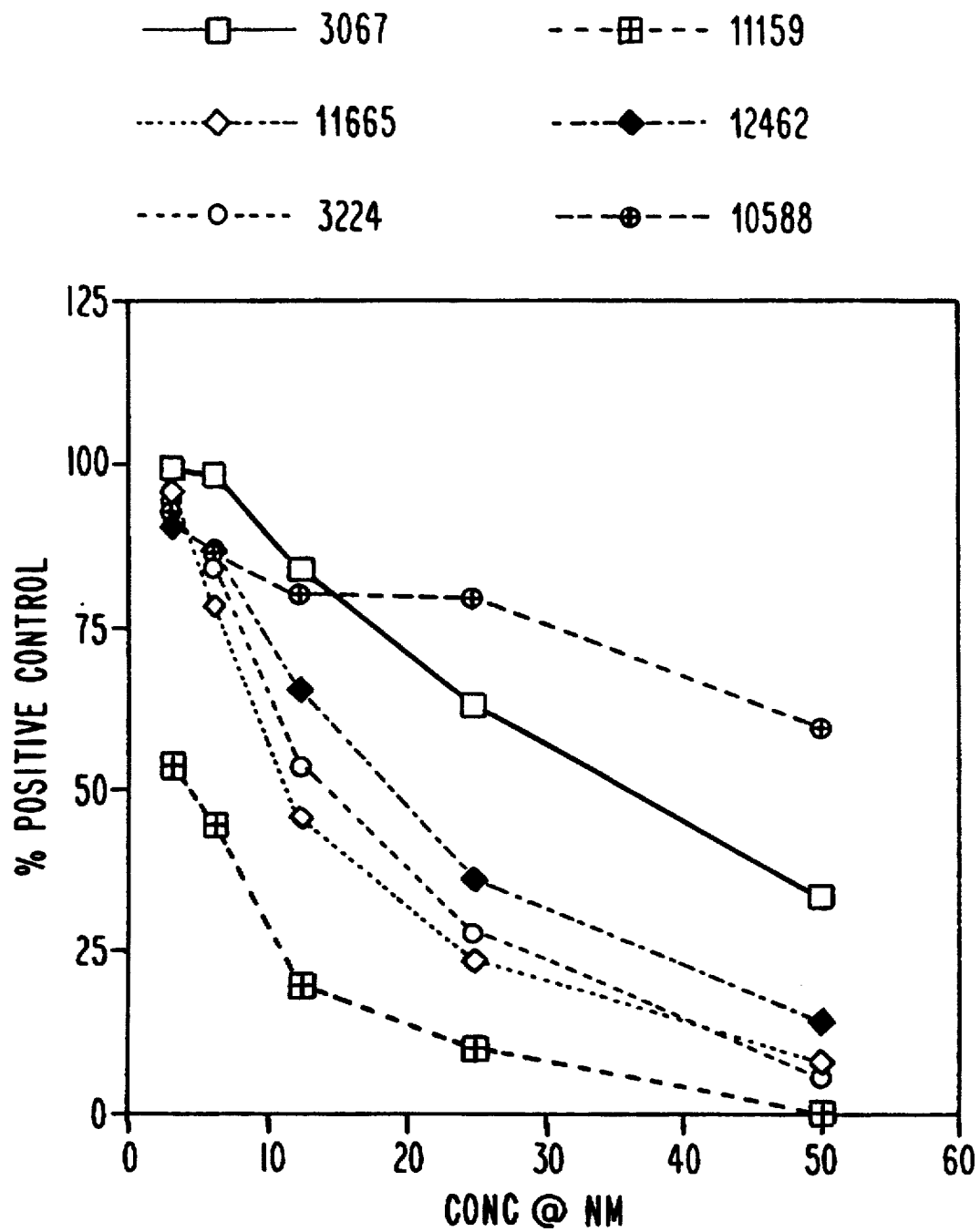
FIG. 1B shows the phosphorothioate compounds.

In the phosphorothioate series (FIG. 1A), the 2'-methoxyethoxy (ISIS 11158) was most potent, and the least potent was the 2'-O-allyl (ISIS 12461). In the phosphorothioate series (FIG. 1B) the most potent oligomer was again the 2'-methoxyethoxy (ISIS 11159) and the least potent was the 2'-deoxy, ISIS 3067, which was included for comparative purposes. Scrambled controls were ISIS 10588 (P=S deoxy), ISIS 12344 (P=O, 2'-methoxyethoxy) and ISIS 12345 (P=S, 2'-methoxyethoxy).

IC50's (dose required for 50% inhibition of ICAM-1 levels) were calculated for some of these compounds. ISIS 3067 (P=S, deoxy) was found to have an IC50 of approximately 20 nM. Of the 2'-modified compounds, ISIS 3224 (P=S, 2'-methoxy) had an IC50 of approximately 24 nM, ISIS 11665 (P=S, 2'-F) had an IC50 of approximately 10 nM and ISIS 11159, (P=S, 2'-methoxyethoxy) had an IC50 of approximately 3 nM. These compounds are preferred. The phosphodiester 2'-methoxyethoxy compound, ISIS 11158, had an IC50 of approximately 9 nM. This compound is also preferred.

Figure 2:
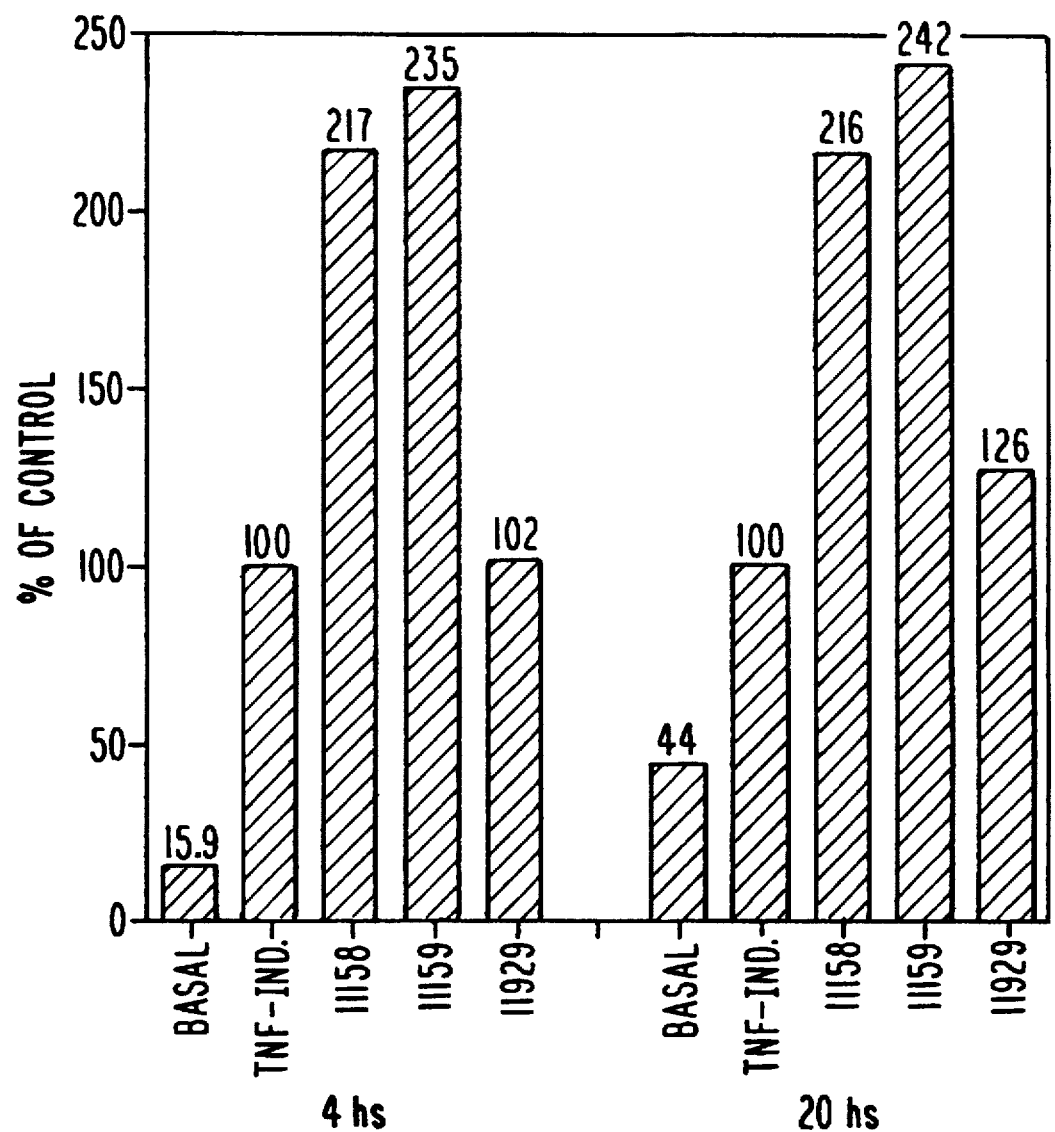
FIG. 2 is a bar graph of a Northern blot showing a significant increase in the relative abundance of the ICAM-1 transcript in cells treated with the anti-ICAM-1 oligonucleomers ISIS 11158 and 11159.

Total cellular RNA was isolated from oligomer-treated HUVECs and analyzed to determine if inhibition of ICAM-1 protein expression resulted from antisense-promoted degradation of the target transcript. Surprisingly, Northern blot analysis showed a significant increase in the relative abundance of the ICAM-1 transcript in cells treated with the anti-ICAM-1 oligonucleotides (ISIS 11158 and 11159). This is shown in FIG. 2. ICAM-1 protein expression was completely inhibited at these oligonucleotide concentrations.

ISIS 11929 is an antisense oligonucleotide targeted to E-selectin, another cellular adhesion molecule, and was included in this experiment as a control. Treatment of cells with ISIS 11929 did not cause an increase in ICAM-1 mRNA levels, but did cause an increase in E-selectin mRNA levels.

Polysome profiles were utilized to determine the effect of antisense oligonucleotide treatment upon translation of the target ICAM-1 transcript. ICAM-1 protein and mRNA levels were measured after treatment with ISIS 11159 or ISIS 12345 (control). Cell surface expression of ICAM-1 protein was determined by FACS analysis of a small portion of treated cells; ISIS 11159 was found to reduce ICAM-1 levels by 84% compared to untreated controls. The scrambled control oligomer ISIS 12345 reduced ICAM expression by only 3%. Cytosolic extracts of the remaining cells were prepared and sedimented by sucrose gradient centrifugation. Gradients were fractionated, RNA was isolated from each fraction and analyzed on a 1% denaturing agarose gel to demonstrate acceptable separation of the subpolysomal and polysomal pools. Determination of the distribution of the ICAM-1 transcript by northern blotting showed a significant difference in the polysome profile for ISIS 11159 treated cells compared to cells treated with the control oligomer ISIS 12345 or untreated control cells. The ISIS 11159 showed the majority (67%) of the full-length ICAM-1 transcript localized in the subpolysome fraction (40S, 60S and 80S ribosome fractions) whereas the control ISIS 12345-treated and untreated cells showed the majority (73% and 69% respectively) of the full length ICAM-1 transcript in the polysome fractions. This demonstrates that ISIS 11159 is interfering with translation directly, by interfering with ribosome assembly onto the target mRNA.

Peptide-nucleic acid (PNA) oligomers targeted to the 5' cap have also been shown to inhibit ICAM-1 expression. A PNA oligomer, ISIS 10535 (SEQ ID NO: 2), was synthesized, which is a shortened version of SEQ ID NO: 1 made as a PNA, with three arginines added at the 5' end and one lysine added at the 3' end. This oligomer was electroporated into U937 cells and a potent dose-response was obtained. ICAM-1 was reduced to below baseline levels at higher doses of ISIS 10535. Under these electroporation conditions, ISIS 10535 had an IC50 of less than 5 µM and ISIS 3067 had an IC50 of over 20 µM. Therefore, ISIS 10535 is preferred.

E-selectin

Other adhesion molecules have been identified which are involved in the adherence of white blood cells to vascular endothelium and subsequent migration out of the vasculature. One of these is E-selectin, also known as endothelial leukocyte adhesion molecule-1 (ELAM-1).

A series of 2'-fluoro phosphorothioate oligonucleotides targeted to human E-selectin were synthesized and tested for ability to inhibit E-selectin protein expression. Of over 30 oligonucleotide sequences complementary to various regions of the E-selectin message (5' cap, 5' UTR, AUG, coding region, intron, 3' UTR), by far the most active was ISIS 9984 (SEQ ID NO: 3; GAAGTCAGCCAAGAACAGCT), targeted to the 5' cap region (nucleotides 1–20) of the human E-selectin mRNA.

Figure 3:
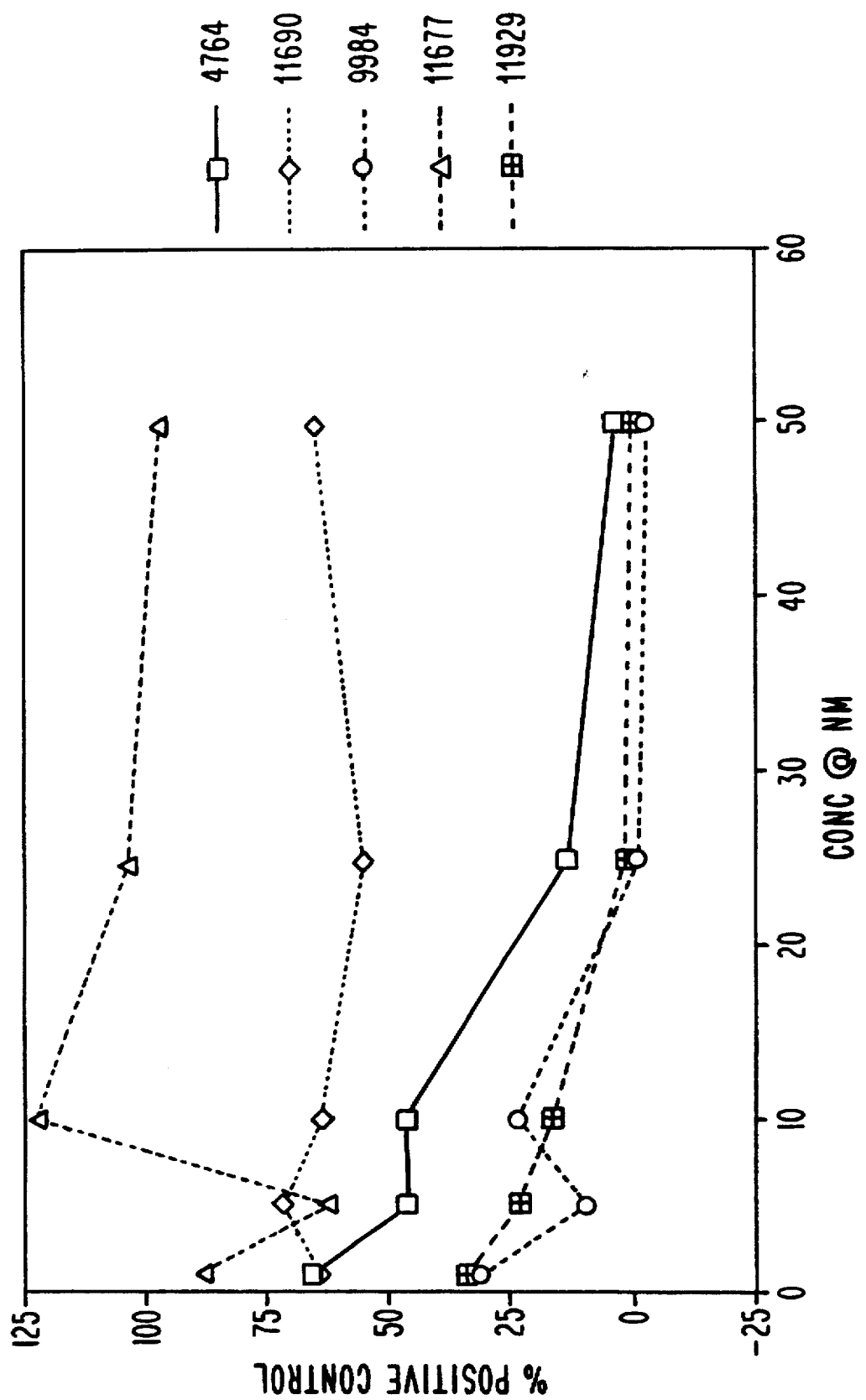
FIG. 3 is a line graph showing the ability of 2' modified oligomers targeted to the 5' cap region of the E-selectin mRNA to inhibit E-selectin expression in HUVECs.

Analogs of this sequence were synthesized with 2'-deoxy, 2'-propoxy, or 2'-methoxyethoxy modifications. These compounds were tested for their ability to inhibit E-selectin expression in HUVECs. As shown in FIG. 3, in this experiment the deoxy phosphorothioate compound, ISIS 4764, had an IC50 of less than 10 nM. The 2'F phosphorothioate analog, ISIS 9984, and the 2'-methoxyethoxy phosphodiester analog, ISIS 11929, both had IC50s well below this and these two compounds are preferred.

Human cytomegalovirus (HCMV)

The human CMV genome is the most complex of the herpes viruses in terms of its genomic structure. Replication-defective mutants of human CMV have only been isolated for two viral genes, the immediate early complex (IE1/IE2) and the DNA polymerase. These genes are known to play major roles in human CMV gene expression. They have been selected as primary targets for antisense compound design.

The molecular biology of immediate early transcription in CMV has been as well elucidated as that of any transcriptional unit in the eucaryotic cell. Briefly, synthesis of the major immediate early transcript (IE1) is controlled by a number of transcriptional response molecules known to operate in cell-specific and differentiation specific manners. The IE1/IE2 mRNA is an abundant capped RNA which encodes both IE1 and IE2 proteins, by differential splicing of the mRNA. IE1 controls the expression of itself as well as that of the IE2 gene product. At the initial phase of immediate early transcription, only IE1 MRNA is synthesized by the cellular RNA polymerase. IE2 mRNA is made by processing of the IE1 mRNA during this early time of infection. The IE2 protein is capable of transcriptionally activating many of the CMV early and late genes in a manner similar to other known transactivating proteins of cellular and viral origin. Thus, the IE2 protein is believed to be one of the master switches for CMV gene expression. An antisense drug targeted to CMV IE2 mRNA, is presently in clinical trials and has been shown to be active against CMV retinitis in AIDS patients.

The sequence of the CMV IE1/IE2 mRNA transcript is known (Stenberg, R. M., Witte, P. R. and Stinski, M. F., *J. Virol.* 1985, 56, 665–675; Stenberg, R. M., Thomsen, D. R., and Stinski, M. F., *J. Virol.* 1984, 49: 190–199). The 5' end of the mRNA is now known to terminate with a "G" (oligonucleotides 1–21 are shown):

CMV IE1/IE2 mRNA 5' end
5' pppGUCAGAUCGCCUGGAGACGCC     SEQ ID NO: 4

Dose-response experiments were done to identify active antisense compounds for inhibition of CMV replication. ISIS 3300, a phosphorothioate oligonucleotide which is fully 2'-methoxy, was found to be active. This compound (SEQ ID NO: 5: TGGCGTCTCCAGGCGATCTGA) is complementary to the 5' cap region (nucleotides 2–22) of the IE1/IE2 transcript and is preferred. Analogs of SEQ ID NO: 5 were also tested for activity against CMV. The modifications, and IC50s for these oligomers, along with parallel controls, are shown in Table 2:

TABLE 2

| 2' modifications of oligonucleotides targeted to the 5' cap of human CMV IE mRNA (SEQ ID NO: 5) | | |
|---|---|---|
| ISIS # | CHEMICAL MODIFICATION | IC50 (µM) |
| 3246 | P=S, deoxy | 0.7 |
| 3300 | P=S, uniform 2'-O—methyl | 0.3 |
| 3300 | P=S, uniform 2'-O—methyl | 0.2 |
| 4155 | P=S, uniform 2'-O—propyl | 0.2 |
| 4952 | P=O, uniform 2'-fluoro | >4.0 |
| 4979 | P=S, uniform 2'-fluoro | 0.6 |
| 3904 | neg. control: P=S, uniform 2'-O—methyl | 3.0 |
| 2922 | pos. control: P=S | 0.2 |

Oligonucleotides having IC50s of 1 µM or below in Table 2 are preferred.

Oligonucleotides were directly tested for ability to inhibit expression of IE1 and IE2 protein products in stably transfected U373 neuroblastoma cells expressing a single CMV protein. IE1 is translated into a 72 kD polypeptide product. IE2 is differentially spliced into two polypeptide products, a 55 kD product and an 86 kD product.

A series of phosphorothioate 2'-methoxy modified oligonucleotides were tested for their ability to inhibit the 55 kD IE2 product. Oligonucleotides (75 nM, 5 µg/ml lipofectin) targeted to the 5' cap region were found to be more active than oligonucleotides targeted elsewhere on the mRNA. ISIS 3300, targeted to nucleotides 2–22 of IE1/IE2 mRNA, inhibited synthesis of the 55 kD product by over 50% at this concentration. ISIS 6871 (GGCGTCTCCAGGCGATCTGAC, SEQ ID NO: 6), targeted to nucleotides 1–21, inhibited synthesis of this product by over 65%. ISIS 12659 (GGCGTCTCCAGGCGATCTGA, SEQ ID NO: 7), targeted to nucleotides 2–21 of the mRNA, inhibited 55 kD levels by approximately 90% and ISIS 12660 (TGGATGGCGTCTCCAGGCGA, SEQ ID NO: 8), targeted to nucleotides 7–26, inhibited 55 kD synthesis by over 75%.

In stable transfectants expressing the 72 kD IE1 protein product, ISIS 3300 (SEQ ID NO: 5) was found to inhibit expression of the 72 kD protein with an IC50 of approximately 75 nM. The methoxyethoxy analog of this oligomer, ISIS 11938, had an IC50 of approximately 25 nM.

Thus antisense oligomers targeting the 5' terminus of the CMV IE1/IE2 mRNA can effectively inhibit synthesis of multiple protein products of this transcript.

While the present invention has been described with specificity in accordance with certain of its preferred embodiments, the following examples serve only to illustrate the invention and are not intended to limit the same.

EXAMPLES

Example 1

Oligonucleotide Synthesis

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle is replaced by a 0.2M solution of $^3$H-1,2-benzodithiole-3-one 1,1-dioxide in acetonitrile for the stepwise thiation of the phosphite linkages. The thiation cycle wait step is increased to 68 seconds and is followed by the capping step.

2'-methoxy oligonucleotides are synthesized using 2'-methoxy β-cyanoethyldiisopropyl-phosphoramidites (Chemgenes, Needham Me.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al., *J. Med. Chem.* 1993, 36, 831–841. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups by was accomplished using standard methodologies and standard methods were used to obtain the 5'-dimethoxytrityl- (DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2, 2'-anhydro-1-β-D-arabinofuranosyluracil was treated with 70% hydrogen fluoride-pyridine. Standard procedures were used to obtain the 5'-DMT and 5'-DMT-3'-phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3 phosphoramidites.

After cleavage from the controlled pore glass column (Applied Biosystems) and deblocking in concentrated ammonium hydroxide at 55° C. for 18 hours, the oligonucleotides are purified by precipitation twice out of 0.5M NaCl with 2.5 volumes ethanol.

2'-(2-methoxyethyl)-modified amidites were synthesized according to Martin, P., *Helv. Chim. Acta* 1995, 78, 486–504. For ease of synthesis, the last nucleotide was a deoxynucleotide. All 2'-O—$CH_2CH_2OCH_3$-cytosines were 5-methyl cytosines.

Synthesis of 5-Methyl cytosine monomers 2,2'-Anhydro [1-(β-D-arabinofuranosyl)-5-methyluridine]:

5-Methyluridine (ribosylthymine, commercially available through Yamasa, Choshi, Japan) (72.0 g, 0.279M), diphenylcarbonate (90.0 g, 0.420M) and sodium bicarbonate (2.0 g, 0.024M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81M), tris(2-methoxyethyl)borate (231 g, 0.98M) and 2-methoxyethanol (1.2 L) were added to a 2 L stainless steel pressure vessel and placed in a pre-heated oil bath at 160° C. After heating for 48 hours at 155°–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506M) was co-evaporated with pyridine (250 mL) and the dried residue dissolved in pyridine (1.3 L). A first aliquot of dimethoxytrityl chloride (94.3 g, 0.278M) was added and the mixture stirred at room temperature for one hour. A second aliquot of dimethoxytrityl chloride (94.3 g, 0.278M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167M), DMF/pyridine (750 mL of a 3:1 mixture prepared from 562 mL of DMF and 188 mL of pyridine) and acetic anhydride (24.38 mL, 0.258M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144M) in CH$_3$CN (700 mL) and set aside. Triethylamine (189 mL, 1.44M) was added to a solution of triazole (90 g, 1.3M) in CH$_3$CN (1 L), cooled to −5° C. and stirred for 0.5 h using an overhead stirrer. POCl$_3$ was added dropwise, over a 30 minute period, to the stirred solution maintained at 0°–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134M) was dissolved in DMF (800 mL) and benzoic anhydride (37.2 g, 0.165M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10M) was dissolved in CH$_2$Cl$_2$ (1 L). Tetrazole diisopropylamine (7.1 g) and 2-cyanoethoxy-tetra-(isopropyl)phosphite (40.5 mL, 0.123M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc⊘Hexane (3:1) as the eluting solvent. The pure fractions were combined to give 90.6 g (87%) of the title compound.

Oligomers having methylene(methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligomers having amide backbones are synthesized according to De Mesmaeker et al., *Acc. Chem. Res.* 1995, 28, 366–374. The amide moiety is readily accessible by simple and well-known synthetic methods and is compatible with the conditions required for solid phase synthesis of oligonucleotides.

Oligomers with morpholino backbones are synthesized according to U.S. Pat. No. 5,034,506 (Summerton and Weller).

Peptide-nucleic acid (PNA) oligomers are synthesized according to P. E. Nielsen et al., *Science* 1991, 254, 1497).

Example 2

Cells and Cell Culture

HUVECs were purchased from Clonetics Corp. (San Diego Calif.) and grown in the suggested EBM medium supplemented with 10% fetal bovine serum (from HyClone, Logan Utah). Cells were used in experiments from passages two to ten at 80–90% confluency.

Example 3

Oligonucleotide Treatment of HUVECs

2×10$^5$ cells/ml were washed three times with OPTI-MEM (Gibco-BRL, Grand Island, N.Y.) prewarmed to 37° C.

oligomers were premixed with 10 µg/ml LIPOFECTIN reagent (Gibco-BRL) in OPTI-MEM, serially diluted to the desired concentrations and applied to washed cells. Basal and untreated (no oligomer) control cells were also treated with LIPOFECTIN. Cells were incubated for 4 hours at 37° C., at which time the medium was replaced with standard growth medium with or without 5 ng/ml TNF-α. In some experiments the cytokine medium was removed after one hour and replaced with standard medium. Incubation at 37° C. was continued until the indicated times.

Example 4

Quantitation of ICAM-1 Protein Expression by Fluorescence Activated Cell Sorting (FACS)

Cells were removed from plate surfaces by brief trypsinization with 0.25% trypsin in PBS. Trypsin activity was quenched with a solution of 2% bovine serum albumin and 0.2% sodium azide in PBS (+Mg/Ca). Cells were pelleted by centrifugation at 1000 rpm (Beckman GPR centrifuge), resuspended in PBS and stained with 3 µl/$10^5$ cells of ICAM-1 specific antibody, CD54-PE (Becton Dickinson, Mansfield Me.) and 0.1 µg of control conjugated antibody, IgG2b-PE (Pharmingen, San Diego Calif.). Antibodies were incubated with the cells for 30 minutes at 4° C. in the dark, under gentle agitation. Cells were washed and then resuspended in 0.3 ml of FACSFLOW buffer (Becton Dickinson) with 0.5% formaldehyde. Expression of cell surface ICAM-1 was then determined by flow cytometry using a Becton Dickinson FACScan (San Jose, Calif.). ICAM-1 expression was calculated as a percentage of control expression.

Example 5

Total RNA Isolation and Northern Analysis

Total cellular RNA was isolated by cellular lysis using CATRIMOX-14 surfactant (Iowa Biotechnology Group, Oakdale Iowa). Isolated RNA was separated on a 1.2% agarose gel containing 1.1% formaldehyde, then transferred to a nylon membrane and UV crosslinked to the membrane using a Stratagene UV crosslinker 2400 (La Jolla Calif.). Blots were hybridized with cDNA probes in QUICKHYB solution (Stratagene). Blots were washed twice at room temperature in 2× SSC with 0.1% SDS for 10 minutes each and then once in 0.1% SSC with 0.1% SDS at 65° C. for 30 minutes.

Example 6

Polysome Profile Analysis

Approximately $10^6$ pelleted cells, washed with PBS, were mixed into 0.3 ml cold lysis buffer (0.5% NP-40, 10 mM Tris-Cl, pH 7.4, 140 mM KCl, 5 mM MgCl$_2$, 1 mM DTT, 100 µg/ml cycloheximide, and Prime RNase inhibitor) and incubated for 5 minutes at 4° C. Nuclei were pelleted at 1000×g, and the resulting supernatant was layered on a 10 to 35% (wt/vol) linear sucrose gradient (4 ml) with a 50% cushion (0.75 ml), in gradient buffer (10 mM Tris pH 8.0, 50 mM KOAc, 1 mM MgOAc, 1 mM DTT). Gradients were centrifuged at 35,000 rpm for 3 hours at 5° C. with a Beckman SW55Ti rotor. 250 µl fractions were collected with an Isco model 185 density gradient fractionator connected to a Pharmacia UV monitor and fraction collector. Collected fractions were treated with proteinase K (0.2 mg/ml) in 0.2% SDS at 42° C. for 20 minutes, phenol-extracted, and ethanol-precipitated. 5 to 10 µg of tRNA was added to each fraction prior to precipitation. Precipitated RNA was applied to a 1.2% denaturing agarose gel, and analyzed by standard ethidium bromide staining and northern blotting techniques.

Example 7

ELISA Screening of Oligomers for Activity Against ELAM-1 Gene Expression

Primary human umbilical vein endothelial (HUVEC) cells, passage 2 to 5, were plated in 96-well plates and allowed to reach confluence. Cells were washed three times with Opti-MEM (GIBCO, Grand Island N.Y.). Cells were treated with increasing concentrations of oligomer diluted in Opti-MEM containing 10 µg/ml DOTMA solution (Bethesda Research Labs, Bethesda Md.) for 4 hours at 37° C. The medium was removed and replaced with EGM-UV (Clonetics, San Diego Calif.) plus oligomer. Tumor necrosis factor α was added to the medium (2.5 ng/ml) and the cells were incubated an additional 4 hours at 37° C.

ELAM-1 expression was determined by ELISA. Cells were gently washed three times with Dulbecco's phosphate-buffered saline (D-PBS) prewarmed to 37° C. Cells were fixed with 95% ethanol at 4° C. for 20 minutes, washed three times with D-PBS and blocked with 2% BSA in D-PBS. Cells were incubated with ELAM-1 monoclonal antibody BBA-1 (R&D Systems, Minneapolis Minn.) diluted to 0.5 µg/ml in D-PBS containing 2% BSA for 1 hour at 37° C. Cells were washed three times with D-PBS and the bound ELAM-1 antibody was detected by incubation with a 1:1000 dilution of biotinylated goat anti-mouse IgG (Bethesda Research Laboratories, Gaithersberg, Md.) in blocking solution for 1 hour at 37° C. Cells were washed three times with D-PBS and then incubated with a 1:1000 dilution of streptavidin conjugated to β-galactosidase (Bethesda Research Laboratories) for 1 hour at 37° C. The cells were washed three times with D-PBS for 5 minutes each. The amount of β-galactosidase bound to the specific monoclonal antibody was determined by developing the plate in a solution of 3.3 mM chlorophenolred-β-D-galactopyranoside, 50 mM sodium phosphate, 1.5 mM MgCl$_2$; pH=7.2 for 2 to 15 minutes at 37° C. The concentration of the product was determined by measuring the absorbance at 575 nm in an ELISA microtiter plate reader.

Example 8

ELISA Assay for Inhibition of HCMV Replication by Antisense Oligonucleotides

Oligonucleotides complementary to human cytomegalovirus mRNA were tested for antiviral activity in an ELISA-based assay of HCMV replication. Normal human dermal fibroblasts (Clonetics Corp., San Diego Calif.) were grown in serum-free medium (Clonetics) and used to seed 96-well plates. When cells were approximately 80% confluent, they were pretreated with oligonucleotides. Approximately 20 hours after pretreatment the medium (containing oligonucleotides) was carefully poured off and the cells washed twice with warmed fibroblast basal medium (FBM, Clonetics). Cells were then infected with 100 µl/well of CMV stock diluted in FBM. The plates were incubated at 37° C. for two hours. The medium (containing virus) was then carefully poured off and replaced with fresh, pre-warmed FBM medium, 100 µl per well. The plates were briefly incubated at 37° C. and then 5 µl of oligonucleotide, diluted in FBM, was reintroduced into the medium in each well. Two days later, cells were post-treated again with oligonucleotides in the same way. On day six, the plates were prepared for ELISA.

In preparation for ELISA, the medium was carefully poured off the plates, and cells were fixed in 200 µl of absolute ethanol per well. Cells were fixed for 30 minutes at room temperature, then ethanol is removed and plates were air-dried. Plates were blocked for one hour prior to ELISA with PBS containing 2% BSA. Blocking solution was removed and 100 μl of an anti-CMV antibody, diluted 1:2000 in PBS with 1% BSA, was added. Cells were incubated in antibody for one hour at 37° C. and washed three times in PBS. The secondary antibody, biotinylated goat anti-mouse IgG (Bethesda Research Labs, Md.), was diluted 1:1000 in PBS with 1% BSA, and incubated with cells for one hour at 37° C. Cells were then washed and incubated for one hour at 37° C. in streptavidin-B-D-galactosidase. Color was developed with chlorophenol red-B-D-galactopyranoside, 20 mg dissolved in 10 ml of 50 mM Na Phosphate, 1.5 mM MgCl2; plates were shaken for 10 minutes and the absorbance was read at 575 nm.

Example 9

Electroporation of PNA into U937 Cells

Cells were washed in PBS and resuspended in PBS at $1\times10^6$ cells/ml. 0.4 ml of suspension was electroporated in a BTX electroporator (San Diego Calif.) set at 1200 μF and 140 V. Cells were cooled on ice and oligomer was added. Cells were plated in pre-warmed medium ten minutes after electroporation and ICAM-1 expression was induced overnight with 5 ng/ml TNFα. ICAM-1 expression was quantitated by FACS as in Example 4.

Example 10

Western Blot Analysis of Inhibition of Expression of IE1 and IE2 Protein Products Stably transfected U373 neuroblastoma cells were used, each expressing a single CMV protein product. Cells were plated at $4.5\times10^5$ cells/well of a 6 well plate to obtain 55–70% confluence the following day. Cells were treated with oligonucleotide at a concentration of 75 nM, with 5 μg/ml lipofectin, in OPTIMEM for 4 hours. Cells were refed with medium without oligonucleotide and allowed to recover overnight. Cells were harvested 16–20 hr post-treatment, washed once with PBS, suspended in Laemmli buffer (100 μl/well), boiled for 5 minutes and loaded on a 16% SDS-PAGE gel. Gels were run for 1.5 hours at 150 V, and transferred to membrane for western blotting. Primary antibody was anti IE 55-72-86 antibody (Virostat) diluted 1:1000 and secondary antibody was radiolabelled goat anti-mouse. Bands were visualized using a PHOSPHORIMAGER (Molecular Dynamics, Sunnyvale Calif.).

---

What is claimed:

1. A composition for inhibiting the translation of a capped target mRNA encoding ICAM-1, E-selectin or CMV IE1/IE2 comprising an oligomer which is 8–25 bases in length and is selected from the group consisting of: an oligonucleotide comprising a modified 2'-position; an oligonucleoside; or a peptide-nucleic acid oligomer;

said oligomer being specifically hybridizable with a 5' cap region of a capped target mRNA which includes at least one of the first 20 nucleotides at the 5' terminus of said target mRNA, and being capable of interfering with ribosome assembly on the mRNA wherein said target mRNA encodes ICAM-1, E-selectin or CMV IE1/IE2.

2. The composition of claim 1 wherein said oligonucleoside comprises at least one morpholino, amide-3, amide-4 or methylene(methylimino) internucleoside linkage.

3. The composition of claim 1 wherein the oligomer has a 2'-OCH$_2$CH$_2$OCH$_3$ modification on each 3'-deoxy sugar moiety.

4. A composition for inhibiting the translation of a capped target mRNA encoding ICAM-1, E-selectin or CMV IE1/IE2 comprising an oligonucleotide having SEQ ID NO: 1 or 2, SEQ ID NO: 3, or SEQ ID NO: 5, 6, 7 or 8, respectively, wherein said oligonucleotide has a 2'-OCH$_2$CH$_2$OCH$_3$ modification on each 3'-deoxy sugar moiety.

* * * * *

UNITED STATES PATENT AND TRADEMARK OFFICE
CERTIFICATE OF CORRECTION

PATENT NO. : 5,789,573
DATED : August 4, 1998
INVENTOR(S) : Baker et al.

It is certified that error appears in the above-indentified patent and that said Letters Patent is hereby corrected as shown below:

At col 2, line 56, please delete "fount" and insert therefore --found--.

At col 3, line 26, please delete "MRNA" and insert therefor --mRNA--.

At col 6, line 24 insert --analog-- after the word methoxyethoxy.

At col 8, line 3, please delete "MRNA" and insert therefor --mRNA--.

At col 12, line 32, please delete "EtOAc0Hexane" and insert therefor --EtOAc\Hexane--.

UNITED STATES PATENT AND TRADEMARK OFFICE
CERTIFICATE OF CORRECTION

PATENT NO. : 5,789,573
DATED : August 4, 1998
INVENTOR(S) : Baker et al.

It is certified that error appears in the above-identified patent and that said Letters Patent is hereby corrected as shown below:

At col 13, line 1, please delete "oligomers" and insert therefor --Oligomers--.

Signed and Sealed this

Second Day of February, 1999

Attest:

Attesting Officer

*Acting Commissioner of Patents and Trademarks*